United States Patent [19]
Anderson et al.

[11] Patent Number: 6,063,773
[45] Date of Patent: *May 16, 2000

[54] CELLULOSE SULFATE FOR USE AS ANTIMICROBIAL AND CONTRACEPTIVE AGENT

[75] Inventors: Robert A. Anderson; Lourens J. D. Zaneveld, both of Chicago, Ill.; Thomas C. Usher, Nassau, Bahamas

[73] Assignees: Polydex Pharmaceuticals Ltd., Nassau, Bahamas; Rush-Presbyterian-St. Luke's Medical Center, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/536,784

[22] Filed: Sep. 29, 1995

[51] Int. Cl.$^7$ .................................................. A61K 31/715
[52] U.S. Cl. .................................................. 514/57
[58] Field of Search ................................. 514/57

[56] References Cited

U.S. PATENT DOCUMENTS

| | | | |
|---|---|---|---|
| 4,840,941 | 6/1989 | Ueno et al. | 514/59 |
| 5,288,704 | 2/1994 | Ungheri et al. | 514/12 |

FOREIGN PATENT DOCUMENTS

| | | | |
|---|---|---|---|
| 0-053 473A | 6/1982 | European Pat. Off. . | |
| 0-116 251A | 8/1984 | European Pat. Off. . | |
| 0298706 | 1/1989 | European Pat. Off. | A61K 31/725 |
| WO 91/15216 | 10/1991 | WIPO | A61K 31/725 |
| WO 95 17898A | 7/1995 | WIPO | A61K 31/70 |

OTHER PUBLICATIONS

Astrup, T. and Alkjaersig, N. (1950) Polysaccharide polysulphuric acids as antihyaluronidases. Nature 166: 568–569.

Spensley, P.C. and Rogers, H.J. (1954) Enzyme Inhibition. Nature 173:1190.

Doring, G.K. (1954) Practical experience with a new vaginal contraceptive. Int. J. Sexol. 8:93–94.

Wood, S.G., Forrest M.E., John, B.A., Chasseaud, L.F. and van de Wiel, J.A.C. (1984) Extent of vaginal absorption of sulphated polysaccharide from A–gen 53 in the rabbit. Contraception 29: 375–383.

Andolz, P., Palazon, X. and Bielsa, M.A. (1983) Estudio del efecto de una nueva asociacion contraceptiva sobre los expermatozozoides humanos. Gine–Dips 11: 1–14.

Hildebrandt, A. (1956) Praktische erfahrungen mit einem fermentchemischen antikonzipiens. Medizinisch Klinik 51: 1192.

Ziegeler, H. (1960) Geburtenkontrolle durch A–GEN 53. Med. Welt 41: 2181.

Martinez–Sausor, V. and Royo A.P. (1984) Estudio de la eficacia y aceptabilldad de un spermicida espermostatico/vaginal en ovulos en portadoras de un disositivo intrauterino. El Medico 91: 82.

Remington's Pharmaceutical Sciences 17$^{th}$ Ed 1985 p. 1158.

Mizumoto et al. "Sulfated homopolysaccharides with immunomodulating activities are more potent anti–HTLV–III agents thatn sulfated heteropolysaccharides " vol. 58, No. 3, 1988.

Yamamoto et al: "synthesis, structure and antiviral activity of sulfates of cellulose and its branched derivatives", vol. 14, No. 1, 1990, pp. 53–64, XP000160254.

Rothschild et al: "endotoxin shock in dogs pretreated with cellulose sulfate" vol. 20, No. 1, 1967, pp. 77–78, XP000645736.

Dunn et al: the reponse of the newborn rat to injury: vol. 116, No. 3, 1975, pp. 165–181, XP000645733.

Zuffrey et al: "risques vrais et faux de la contraception locale" vol. 14, No. 3, 1985, pp. 359, 363, XP000645734.

Zuffrey et al, 1985 J. Gynecol, Obstet Biol Reprod vol. 14 pp. 359–363.

Polsly et al 1988, The Lancet, Jun. 25, p. 1456.

Asculai et al, 1978, Antimicrobial Agent & Chemother vol. 13 (4) pp. 686–690.

*Primary Examiner*—Russell Travers
*Attorney, Agent, or Firm*—Oliff & Berridge, PLC

[57] ABSTRACT

The present invention relates to a method of reducing the risk of infections and the risk of conception. In particular, the invention relates to cellulose sulfate having contraceptive and anti-microbial properties. Cellulose sulfate may be administered in appropriate dosage forms to reduce the risk of infections or the risk of conception. It can also be used during sexual contact to concomitantly reduce the risk of conception and the risk of sexually transmitted diseases.

32 Claims, 9 Drawing Sheets

Figure 1 - Fertilization Outcome After Artificial Insemination of Spermatozoa Pretreated with Different Polysaccharides[A]

| Group | Rabbits/Group | Oocytes/Group | % Fertilization (90% Conf. Limits) |
|---|---|---|---|
| Control | 5 | 33 | 90 (71 - 99) |
| Heparin 100 µg/ml | 3 | 48 | 93 (41 - 100) |
| Heparin 500 µg/ml | 1 | 31 | 87 |
| Dextran Sulfate 10 mg/ml | 1 | 19 | 89 |
| Cellulose Sulfate 1 mg/ml | 2 | 42 | 1 (0 - 11) |
| Cellulose Sulfate 10 mg/ml | 2 | 49 | 0 (0 - 0) |

[A] In each of five separate experiments, spermatozoa were obtained from two pooled ejaculates, separated from seminal plasma by centrifugation through 11% Ficoll, and resuspended in BWW medium. The sperm suspension was divided into two portions. To one portion was added polysaccharide at a final concentration, as indicated. The other portion received an equal volume of BWW medium. After 15 minutes at 37° C, superovulated female rabbits (ages 8 to 11.5 months) were artificially inseminated with either of the two sperm suspensions (ranging from 15 - 25 x $10^6$ sperm per rabbit). Twenty-four hours after insemination, eggs were recovered from the oviducts of the females, and were scored for fertilization. Each experiment contained 1 control rabbit and from 1-3 polysaccharide-treated rabbits. The average % fertilization per rabbit was calculated for each experiment.

Figure 2 - Contraceptive Efficacy of Vaginally Applied
Cellulose Sulfate[A]

| Compound | % Fertilization[B] |
|---|---|
| K-Y Jelly (n = 3) | 82 (65.6 - 94.0) |
| Nonoxynol-9 (n = 3) | 1 (-0.3 - 8.0) |
| Cellulose Sulfate (n = 5) | 0 (-0.2 - 1.2) |

[A]  Compounds were applied vaginally to New Zealand white rabbit 5 minutes prior to artificial insemination with 15 - 17 x $10^6$ washed spermatozoa, obtained from pooled ejaculates (2). Volume of vaginal application was 1.5 ml. Nonoxynol-9 was the active ingredient of a commercial preparation, comprising 2.2% by weight. Vehicle for this formulation was K-Y jelly. Cellulose sulfate was applied as a 5.0% aqueous solution to which were added small amounts of preservative agents. The formulation was prepared and provided by Polydex Pharmaceuticals. Twenty-four hours after insemination, eggs were recovered from the oviducts and scored for fertilization. Sample number refers to the number of rabbits inseminated with each formulation. Total number of eggs examined were 58, 108 and 134 for the K-Y jelly, N-9 and cellulose sulfate groups, respectively.

[B]  Values represent the average fertilization outcome (percent of recovered eggs)) per rabbit. All data were subjected to arcsine transformation prior to calculation of averages and 90% confidence limits (in parentheses).

Figure 3: Cervical Mucus Penetration Test

| Compound | Initial Conc. | % of Control |
|---|---|---|
| Cellulose sulfate | 10 mg/ml | 58.1% ± 9.9 |
| Dextran sulfate | 10 mg/ml | 85.8 ± 3.9 |
| Saline | | 100 |

The end of Sereno Penetrak tube containing lyophilized cow cervical mucus was immersed into 250 ml of a test solution. The concentration of the test solution is indicated above as "initial" concentration. The tube was removed after 30 minutes and 50 ml of semen added to the test solution. The end of the Sereno Penetrak tube was reimmersed into the test solution containing the semen for one hour. The tube was then removed and the migration distance of the most advanced motile spermatozoon was determined microscopically. The migration distance is expressed as a percentage of that of the migration of control spermatozoa in saline test solution.

Figure 4 - Influence of Different Polymeric Compounds on the
Human Acrosome Reaction[A]

| Compound | % $AR_{max}$ [B] |
|---|---|
| Heparin (n = 4) | 48.3 (41.92 - 54.80)[C] |
| Dextran sulfate (n = 3) | 55.0 (52.94 - 57.05)[C] |
| Cellulose sulfate (n = 4) | 102.4 (99.8 - 111.7)[D] |

[A] Compounds were evaluated as stimuli of the acrosome reaction of noncapacitated human spermatozoa at a concentration of 0.5 μg/ml. Prior experiments determined that this concentration was the approximate $ED_{50}$ for the acrosome reaction induced by heparin (actual $ED_{50}$ = 0.38 μg/ml, determined by TableCurve curve-fitting software on a dose-response curve for heparin).

[B] Values are expressed as the percentage of the acrosome reaction in response to a maximally stimulating concentration of A23187 (1 nM), with the 90% confidence limits indicated in parentheses.

[C-D] Values with different superscripts differ ($p < 0.05$, Newman-Keuls multiple range test).

Figure 5: Prevention of Human Immunodeficiency Virus (HIV) Infectivity by Cellulose Sulfate

TESTING CONCENTRATIONS

| Compound | Solvent | 1.0% | 0.5% | 0.1% | 0.05% | 0.01% | 0.005% | 0.001% |
|---|---|---|---|---|---|---|---|---|
| Cellulose Sulfate | PBS | P[100.00] | P[100.00] | P[100.00] | 100.00 | 100.00 | 100.00 | 54.9 |

Results are expressed as percentage of viral infectivity reduction

P:Partial toxicity. In parenthesis percentage of inhibition

Cultures of MT2 cells (plated in 96 well cell culture plates at 10,000 cells per well) were grown in RPMI 1640 medium, supplemented with 10% fetal bovine serum, 100 I.U./ml penicillin, 100 μg/ml streptomycin, 20 μg/ml gentamicin and 25 mM HEPES. Serial dilutions of test compound were added to HIV-1 (strain 111$_s$), propagated in a T4-lymphoblastoid cell line, harvested, and diluted, such that 50μl inoculum produced 70-100 syncytia per well, in untreated MT2 cell cultures. Each serial dilution of compound with virus was added to each of 3 wells containing the MT2 cells. A fourth well contained only test compound, and served as a screen for possible cytotoxicity. Virus control samples (no compound added) were also included, in triplicate. The virus control wells received an equal volume of RPMI medium used to dissolve the test compound. The virus/cell cocultures were incubated at 37° (5% CO$_2$) for 48-72 hours. At this time, cultures were scored microscopically for syncytia formation at each dilution of test compound. Infectivity of HIV in vitro was completely inhibited by cellulose sulfate at a concentration of 0.5 mg/ml. At higher concentrations, the cellulose sulfate showed partial cytotoxicity toward the T4 cell line (designated by 'P').

Figure 6: Prevention of Infectivity of Herpes Simplex Virus
(HSV) By Cellulose Sulfate Cellulose Sulfate

|  | PFU / Plate | | | |
|---|---|---|---|---|
| Dose ($\mu$g/ml) | Virus Conc. (1) (DF 1.8 x $10^5$ | Virus Conc. (1/10) (DF 1.8 x $10^6$ | Titer | % of Control |
| 0 | TNTC | 168,152,187 | 3.04 x $10^8$ | (100) |
| 0.1 | (NA) | 46,55,37 | 8.3 x $10^7$ | 27.2 |
| 1.0 | 116,109,90 | 1,2,3 | 1.9 x $10^7$ | 6.21 |
| 10 | 9,10,14 | 1,2,1 | 2.0 x $10^4$ | 0.65 |
| 100 | 7,10,10 | 1,0,1 | 1.6 x $10^6$ | 0.53 |
| 500 | 9,10,9 | 1,2,3 | 1.7 x $10^6$ | 0.55 |

TNTC = Too numerous to count

Cellulose sulfate was serially diluted in phosphate-buffered saline (PBS), and each dilution was mixed with HSV (type 2, strain 333). Samples (1 ml) of each mixture were plated in triplicate on washed and drained monolayers of Vero (African green monkey kidney) cells on the bottoms of 25 $cm^2$ flasks. Initial titer (indicated in the control cultures with no added cellulose sulfate) in each culture is given as plaque forming units per ml. The flasks were incubated for 2 hours, after which, the medium (containing virus and test compound) was removed, and the cells were washed with PBS. Cells were cultured in supplemented medium 199 for 3 days. Cells were then stained with Geimsa for the counting of viral plaques. The viral titer was inferred from the number of plaques. Data are also expressed as the percentage of plaques that were counted in control cell cultures (not exposed to cellulose sulfate). The concentration of cellulose sulfate that is required to reduce the viral titer by 50% is estimated at 0.028 $\mu$g/ml.

Figure 7: Prevention of Replication of Neisseria Gonorrhea
by Cellulose Sulfate

|  | COLONY FORMING UNITS |
|---|---|
| INOCULUM | $1.9 \times 10^7$ |
| CONTROL | $1.3 \times 10^8$ |
| CELLULOSE SULFATE | |
| 100 µg/ml | 0.0 |
| 10 µg/ml | $4.4 \times 10^7$ |
| 1.0 µg/ml | $2.5 \times 10^7$ |
| 0.1 µg/ml | $7.0 \times 10^7$ |

Neisseria gonorrhea from local uncomplicated cases of gonorrhea were isolated (verified by Gram stain, oxidase reactivity and sugar fermentation). The titer of log-phase cultures were adjusted by dilution in GC broth to 0.5 McFarland standard (approximately $10^8$ colony forming units per ml). This was diluted 1:10 with broth containing no additions (control), and each of serial 1:10 dilutions of cellulose sulfate, ranging from 100 µg/ml to 0.1 µg/ml. The suspensions were incubated at 37° for four hours. Five serial 1:10 dilutions were made in GC broth, and 20 µl from each dilution were inoculated onto GC agar plates. The plates were incubated overnight, and resultant gonococcal colonies were counted. Data for each concentration of cellulose sulfate are expressed as the number of colony-forming units per ml of the original log-phase bacterial suspension. The actual initial inoculum used in each plate (based on colony count of the control plate) is presented in the table. The data show a dose-dependent decrease in bacterial cell count due to cellulose sulfate. The concentration of cellulose sulfate required to inhibit gonococcal growth by 50% is 4 µg/ml.

Figure 8 - Failure of Cellulose Sulfate to Inhibit Growth of a Vaginal Strain of Lactobacillus

| Additions | Cell Cycle Length ($T_D$, or 'Doubling Time', in minutes) | 90% Confidence Limits |
|---|---|---|
| None (Control) | 110 | 98-126 |
| 1.8% Cellulose Sulfate | 110 | 102-118[a] |
| Pen/Strep | 356 | 320-401[b] |

Lactobacillus gasseri, obtained from the American Type Culture Collection (Rockville, MD) was cultured under anaerobic conditions at 37° in the presence of either 1.8% cellulose sulfate, a commercial pen/strep solution (final concentration of penicillin G = 1 Unit/ml; final concentration of streptomycin = 1 µg/ml), or no additions (control). Beginning at 120 minutes after the start of incubation and at 20 minute intervals, for a total length of 200 minutes, samples were removed from the incubation flasks, and the absorbance of the suspension at 550 nm was determined, as an estimate of cell density. Data were fit to the equation, Ln (Absorbance) = a + b (Time), where a is the absorbance at 0 time, b is the slope of the curve, and time is measured in minutes. The doubling time ($T_D$) was calculated from the equation $T_D$ = (Ln 2)/b. Values are given as the doubling time of bacterial growth, together with the 90% confidence limits.

[a] Value is not different from control ($p > 0.10$).

[b] Value differs from control ($p < 0.01$).

Figure 9: Anti-chlamydial Effect of Cellulose Sulfate

| Concentration of Cellulose Sulfate | Log (inclusion forming units) |
| --- | --- |
| Control (0 μg/ml) | 7.41 |
| 10 μg/ml | 6.72 |
| 100 μg/ml | 6.38 |

C. trachomatis (EBs) were mixed with each of cellulose sulfate and control and incubated for 2 hours. The incubates were then added to HeLa cells and incubated for 1 hour. The supernatant containing EBs was removed and culture media added to the HeLa cells. 48 hours later, the number of HeLa cells having inclusions was determined using fluorescent antibodies.

CELLULOSE SULFATE FOR USE AS ANTIMICROBIAL AND CONTRACEPTIVE AGENT

FIELD OF INVENTION

The present invention relates to a pharmaceutical composition and method for reducing the risk of conception and transmission of infectious agents during sexual contact. In particular, it relates to a composition comprising cellulose sulfate having contraceptive and anti-microbial and anti-viral properties.

BACKGROUND OF THE INVENTION

Various contraceptive methods are known for reducing the risk of conception. The condom is a contraceptive method developed for use by men, and is known to reduce the risk of contracting sexually transmitted diseases. Presently, no contraceptive method for use by women is generally known to be effective in reducing the risk of contracting sexually transmitted diseases such as gonorrhea, herpes and more recently, AIDS.

Contraceptive methods currently available to and under the control of women include oral contraceptives, diaphragm, intrauterine devices and vaginal foams, creams and suppositories. Each one of the vaginal formulations utilizes a cytotoxic agent, usually the detergent nonoxynol-9, as active ingredient. A vaginal suppository containing sulphuric acid ester of a polysaccharide (SAEP) in combination with nonoxynol-9 is also known. SAEP is a sulfated polysaccharide with a molecular weight of about 175,000. It inhibits hyaluronidase, an enzyme which is believed to have an indispensable role in fertilization. Nonoxynol-9, if used frequently causes irritation to the mucus membrane of the vagina, inactivates the natural protective vaginal flora and can cause lesions through which an infectious agent can invade and cause infection.

Sexually transmitted diseases, and in particular, AIDS, caused by the Human Immunodeficiency Virus (HIV), present a serious health risk. It is therefore important to develop a method which avoids the vaginal irritation and the nonspecific inactivation of the naturally occurring vaginal microbes while providing protection against infectious microbes and unwanted pregnancies. Several such agents which are noncytotoxic or of low cytotoxicity are known to inhibit HIV infectivity in vitro, such as select sulfated polysaccharides including dextran sulfate and heparin sulfate. Some sulfated polysaccharides are also known to inhibit Herpes Simplex Virus (HSV), including dextran sulfate of relatively high molecular weight. As well, heparin sulfate has been shown to inhibit HSV infectivity. However, these sulfated polysaccharides shown to have anti-viral activity are not known to have contraceptive properties.

Accordingly, there is a need for a contraceptive for use by women, and as an alternative to the use of the condom, which also reduces the risk of contraction of sexually transmitted diseases.

SUMMARY OF THE INVENTION

According to an aspect of the present invention, there is provided a method for at least one of reducing the risk of infections and treating infections comprising administering an effective amount of cellulose sulfate.

There is also provided a method for concomitantly reducing the risk of conception and at least one of reducing the risk of infections and treating infections comprising administering an effective amount of cellulose sulfate.

Yet in another aspect of the invention, there is provided a method for reducing the risk of conception comprising administering an effective amount of cellulose sulfate, with a molecular weight of at least 500,000.

In another aspect of the invention, there is provided a method for at least one of reducing risk of infections and treating infections comprising administering a pharmaceutical composition said composition comprising an effective amount of cellulose sulfate.

There is also provided a method for concomitantly reducing risk of conception and at least one of reducing risk of infections and treating infections comprising administering a pharmaceutical composition said composition comprising an effective amount of cellulose sulfate.

In another aspect of the invention, there is provided a method for reducing risk of conception comprising administering a pharmaceutical composition said composition comprising an effective amount of cellulose sulfate, with a molecular weight of at least 500,000.

Yet in another aspect of the invention, there is provided a cellulose sulfate for use in at least one of reducing risk of infections and treating infections.

There is also provided a cellulose sulfate for use in concomitantly reducing risk of conception and at least one of reducing risk of infections and treating infections.

There is provided a cellulose sulfate for use in reducing risk of conception wherein said cellulose sulfate has a molecular weight of at least 500,000.

In another aspect of the invention, there is provided a pharmaceutical composition comprising an effective amount of cellulose sulfate for use in at least one of reducing the risk of infections and treating infections.

Yet in another aspect of the invention, there is provided a pharmaceutical composition comprising an effective amount of cellulose sulfate for use in concomitantly reducing the risk of conception and at least one of reducing the risk of infections and treating infections.

There is also provided a pharmaceutical composition comprising an effective amount of cellulose sulfate for use in reducing the risk of conception wherein said cellulose sulfate has a molecular weight of at least 500,000.

BRIEF DESCRIPTION OF THE DRAWINGS

FIG. 1 is a table showing fertilization outcome after artificial insemination of spermatozoa pretreated with different polysaccharides.

FIG. 2 is a table showing the contraceptive efficacy of cellulose sulfate when applied vaginally.

FIG. 3 is a table providing the results of cervical mucus penetration experiments.

FIG. 4 is a table illustrating the influence of cellulose sulfate on acrosome reaction of human spermatozoa.

FIG. 5 is a table illustrating the results of HIV inhibition assay experiments.

FIG. 6 is a table providing the results of HSV infectivity experiments.

FIG. 7 is a table illustrating the effects of cellulose sulfate on the infectivity of *N. gonorrhea*.

FIG. 8 is a table illustrating the effects of cellulose sulfate on the growth of Lactobacilli.

FIG. 9 is a table illustrating anti-chlamydial effects of cellulose sulfate.

DETAILED DESCRIPTION OF THE PREFERRED EMBODIMENTS

Cellulose sulfate of the present invention has preferably a molecular weight of at least 500,000 and is maximally sulfated (about 17% by weight). It has been found that cellulose sulfate is effective in reducing the risk of conception. Upon vaginal application, or upon pre-treatment of spermatozoa preparations, cellulose sulfate inhibits conception in rabbits. It has also been found that cellulose sulfate is effective in reducing the risk of the infection of human cells growing in vitro by various viruses. It can also be used to inhibit replication of bacteria which are foreign to the normal vaginal flora. Therefore, the present invention provides a contraceptive which also reduces the risk of transmission of infectious agents during sexual contact.

The present invention may be administered in an effective amount in suitable dosage forms such as vaginal or rectal gels, foams, creams, suppositories or aerosols. Cellulose sulfate of the present invention may also be administered in combination with a known spermicide such as nonoxynol-9. Suitable carriers, diluents and other non-active ingredients generally known to those skilled in the relevant art may also be combined with cellulose sulfate or cellulose sulfate and nonoxynol-9.

Contraceptive Effect:

FIG. 1 illustrates the antifertility effect of cellulose sulfate on rabbit spermatozoa at a concentration as low as 0.1%. Pre-treatment of spermatozoa with 1% cellulose sulfate effectively prevented conception in rabbits inseminated with treated spermatozoa. On the other hand, treating spermatozoa with heparin or dextran sulfate showed little or no anti-fertility effect.

Referring to FIG. 2, a 5% cellulose sulfate formulation when applied intra-vaginally in rabbits reduces the risk of conception. A comparison of the percentage of fertilized oocytes observed from rabbits treated with 5% cellulose sulfate and 2.2% commercial preparation of nonoxynol-9 indicates that cellulose sulfate of the present invention is as effective or more effective than nonoxynol-9 in reducing the risks of conception when applied intravaginally.

Cellulose sulfate, when administered vaginally to rabbits, causes minimal vaginal irritation. When applied in combination with nonoxynol-9, cellulose sulfate of the present invention does not cause an increase in the vaginal irritation of nonoxynol-9.

Referring to FIG. 3, experimental results indicate that at 1% concentration, cellulose sulfate impedes penetration by spermatozoa into the cervical mucus membrane in vitro, and to a significantly greater extent than dextran sulfate at the same concentration.

With reference to FIG. 4, cellulose sulfate of the present invention also induces acrosomal loss in human spermatozoa, and to a significantly greater extent than heparin or dextran sulfate. Acrosome refers to the anterior organelle of the sperm head necessary for fertilization of an egg by the sperm.

From the foregoing results, as described in FIGS. 1–4, it will be apparent to one skilled in the art that cellulose sulfate of the present invention, in effective amounts, can be used to reduce the risk of conception in humans.

Anti-viral and Anti-microbial Effects:

Referring to FIG. 5, the experimental results indicate that cellulose sulfate at concentration of 0.005% inhibits the binding of HIV to human cells in vitro.

FIG. 6 illustrates that at concentration as low as 0.00001%, cellulose sulfate of the present invention inhibits infection of human cells by HSV in vitro.

With reference to FIG. 7, the experimental results indicate that, cellulose sulfate at a concentration of at least 0.01% can completely kill the bacteria *N. gonorrhea*. Moreover, cellulose sulfate of the present invention at 1.8% has no effect on normal vaginal flora, namely Lactobacilli (FIG. 8).

FIG. 9 illustrates anti-chlamydial effect of cellulose sulfate. At a concentration of 100 μg/ml, cellulose sulfate inhibits chlamydial infection of HeLa cells by 91%.

The forgoing results, as described in FIGS. 5 and 6, indicate that the addition of cellulose sulfate in a concentration as low as 0.00001% is effective in inhibiting the infection of human cells by viral pathogens in vitro. Furthermore, the forgoing results, as described in FIGS. 7–9, indicate that cellulose sulfate can inhibit infection caused by bacteria which are foreign to normal vaginal flora.

Accordingly, it will be apparent to one skilled in the art that cellulose sulfate in effective amounts can be used in humans to reduce the risk of or treat viral and microbial infections. In particular, cellulose sulfate of the present invention will be useful as vaginal, rectal and other topical (including dermatological) applications.

The forgoing detailed description is for the purposes of illustration only and is not intended as limiting the scope of the invention. Persons skilled in the art will appreciate the nature and the scope of the invention including all of its practical applications.

What is claimed is:

1. A method of treating bacterial infection comprising administering an effective amount of cellulose sulfate to a patient in need of such treatment.

2. The method according to claim 1, wherein said bacterial infection is sexually transmitted.

3. The method according to claim 2, wherein said bacterial infection is caused by *N.gonorrhea*.

4. The method according to claim 1, wherein said cellulose sulfate is maximally sulfated.

5. The method according to claim 1, wherein said cellulose sulfate has a molecular weight of at least 500,000.

6. The method according to claim 1, wherein said cellulose sulfate is administered topically.

7. The method according to claim 1, wherein said cellulose sulfate is administered vaginally.

8. The method according to claim 1, wherein said cellulose sulfate is administered rectally.

9. A method according to claim 1 wherein said cellulose sulfate is administered in admixture with a pharmaceutically acceptable diluent or carrier.

10. A method of treating *C. trachomatis* infection comprising administering an effective amount of cellulose sulfate to a patient in need of such treatment.

11. The method according to claim 10, wherein said cellulose is maximally sulfated.

12. The method according to claim 10, wherein said cellulose sulfate has a molecular weight of at least 500,000.

13. The method according to claim 10, wherein said cellulose sulfate is administered topically.

14. The method according to claim 10, wherein said cellulose sulfate is administered vaginally.

15. The method according to claim 10, wherein said cellulose sulfate is administered rectally.

16. A method according to claim 10, wherein said cellulose sulfate is administered in admixture with a pharmaceutically acceptable diluent or carrier.

17. A method of preventing bacterial infection comprising administering an effective amount of cellulose sulfate to a patient in need of such treatment.

18. The method according to claim 17, wherein said bacterial infection is sexually transmitted.

19. The method according to claim 18, wherein said bacterial infection is caused by *N. gonorrhea*.

20. The method according to claim 17, wherein said cellulose sulfate is maximally sulfated.

21. The method according to claim 17, wherein said cellulose sulfate has a molecular weight of at least 500,000.

22. The method according to claim 17, wherein said cellulose sulfate is administered topically.

23. The method according to claim 17, wherein said cellulose sulfate is administered vaginally.

24. The method according to claim 17, wherein said cellulose sulfate is administered rectally.

25. The method of claim 17, wherein said cellulose sulfate is administered in admixture with a pharmaceutically acceptable diluent or carrier.

26. A method of preventing *C. trachomatis* infection comprising administering an effective amount of cellulose sulfate to a patient in need of such treatment.

27. The method according to claim 26, wherein said cellulose is maximally sulfated.

28. The method according to claim 26, wherein said cellulose sulfate has a molecular weight of at least 500,000.

29. The method according to claim 26, wherein said cellulose sulfate is administered topically.

30. The method according to claim 26, wherein said cellulose sulfate is administered vaginally.

31. The method according to claim 26, wherein said cellulose sulfate is administered rectally.

32. The method according to claim 26, wherein said cellulose sulfate is administered in admixture with a pharmaceutically acceptable diluent or carrier.

* * * * *